United States Patent
Harada

(10) Patent No.: US 12,396,622 B2
(45) Date of Patent: Aug. 26, 2025

(54) ENDOSCOPE

(71) Applicant: FUJIFILM Corporation, Tokyo (JP)

(72) Inventor: Takashi Harada, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 755 days.

(21) Appl. No.: 17/392,267

(22) Filed: Aug. 3, 2021

(65) Prior Publication Data

US 2021/0361145 A1 Nov. 25, 2021

Related U.S. Application Data

(63) Continuation of application No. PCT/JP2020/008155, filed on Feb. 27, 2020.

(30) Foreign Application Priority Data

Mar. 1, 2019 (JP) ................. 2019-037792

(51) Int. Cl.
| | | |
|---|---|---|
| *A61B 1/00* | (2006.01) | |
| *A61B 1/018* | (2006.01) | |
| *A61B 1/12* | (2006.01) | |

(52) U.S. Cl.
CPC ...... *A61B 1/00101* (2013.01); *A61B 1/00091* (2013.01); *A61B 1/00098* (2013.01); *A61B 1/018* (2013.01); *A61B 1/126* (2013.01)

(58) Field of Classification Search
CPC ............ A61B 1/00101; A61B 1/00091; A61B 1/00098; A61B 1/018; A61B 1/126; A61B 1/00177; A61B 1/0676
USPC ....................................................... 600/107
See application file for complete search history.

(56) References Cited

U.S. PATENT DOCUMENTS

| | | | | |
|---|---|---|---|---|
| 9,913,574 B2 * | 3/2018 | Surti | ............... | A61B 1/0008 |
| 2018/0242832 A1 * | 8/2018 | Morimoto | .......... | A61B 1/00177 |

FOREIGN PATENT DOCUMENTS

| | | | | |
|---|---|---|---|---|
| JP | 2001000389 | | 1/2001 | |
| JP | 2006223714 | | 8/2006 | |
| JP | 2008086649 | * | 4/2008 | ............... A61B 1/00 |
| JP | 2010115428 | | 5/2010 | |

(Continued)

OTHER PUBLICATIONS

JP2008086649 English Translation (Year: 2008).*

(Continued)

*Primary Examiner* — Michael J Carey
*Assistant Examiner* — Megan Elizabeth Monahan
(74) *Attorney, Agent, or Firm* — JCIPRNET

(57) ABSTRACT

Provided is an endoscope capable of improving operability of the endoscope. An endoscope (10) includes: an observation optical system (76) that is disposed on a wall portion (68) of a distal end portion main body (32) adjacent to an elevator housing portion (66) and that observes a visual field region in a first direction in which the elevator housing portion (66) is open; an outflow port (45) that is provided in the distal end portion main body (32) and through which liquid flows out; and a cap (34) that is attachably and detachably attached to the distal end portion main body (32) and that has a liquid guiding surface that guides the liquid flowing out from the outflow port (45) in a direction toward the visual field region in a state where the cap (34) is attached to the distal end portion main body (32).

10 Claims, 15 Drawing Sheets

(56) References Cited

FOREIGN PATENT DOCUMENTS

| JP | 2012157478 | 8/2012 |
| JP | 2015029764 | 2/2015 |

OTHER PUBLICATIONS

"International Search Report (Form PCT/ISA/210) of PCT/JP2020/008155," mailed on Apr. 21, 2020, with English translation thereof, pp. 1-5.

"International Preliminary Report On Patentability (Form PCT/IPEA/409) of PCT/JP2020/008155," completed on Aug. 7, 2020, with English translation thereof, pp. 1-7.

* cited by examiner

ENDOSCOPE

CROSS-REFERENCE TO RELATED APPLICATIONS

The present application is a Continuation of PCT International Application No. PCT/JP2020/008155 filed on Feb. 27, 2020 claiming priority under 35 U.S.C § 119(a) to Japanese Patent Application No. 2019-037792 filed on Mar. 1, 2019. Each of the above applications is hereby expressly incorporated by reference, in its entirety, into the present application.

BACKGROUND OF THE INVENTION

1. Field of the Invention

The present invention relates to an endoscope, and particularly to an endoscope comprising, at a distal end portion of an insertion part, an elevator that changes a lead-out direction of a treatment tool and a jetting portion that jets liquid toward a visual field region of the endoscope.

2. Description of the Related Art

In an endoscope, various treatment tools are led in from a treatment tool lead-in port provided in a hand operation part, and the treatment tools are led out to the outside from an elevator housing portion that is open at a distal end portion of an insertion part and are used for a treatment. For example, a treatment tool such as forceps or a contrast tube is used for a duodenoscope, and a treatment tool such as a puncture needle is used for an ultrasonic endoscope.

In such a treatment tool, in order to provide a treatment at a desired position in a subject, it is necessary to change a lead-out direction of the treatment tool led out from the elevator housing portion. Therefore, an elevator (also referred to as a raising base) is rotatably provided in the elevator housing portion, and a treatment tool operating member that changes a posture of the elevator between an elevating position and a lying position is provided in the hand operation part (see JP2015-29764A).

JP2015-29764A discloses an endoscope having a liquid jetting device that jets liquid toward a visual field region of the endoscope.

The endoscope of JP2015-29764A has a raising base housing recessed portion that is recessed in a vicinity of a distal end portion of an insertion part with an opening surface facing sideways, a raising base supported in the raising base housing recessed portion so as to be raised and laid down, and a water supply pipe line that supplies liquid, and a send-out port of a distal end of the water supply pipe line is open in the raising base housing recessed portion. When the raising base is raised, a track of water sent from the send-out port of the water supply pipe line overlaps the raising base, and a direction of water supply is changed by a water supply guiding surface of the raising base.

The water supply guiding surface of the raising base of JP2015-29764A has a center part formed into a deep groove shape, and this water supply guiding surface also functions as a guiding surface for leading out the treatment tool to the outside.

SUMMARY OF THE INVENTION

In the field of an endoscope that uses a treatment tool, there is a demand for treating an observation site using the treatment tool while washing the observation site by jetting liquid to the observation site in order to ensure a clear image of the observation site.

However, the endoscope of JP2015-29764A cannot simultaneously perform a liquid supply operation and a treatment tool lead-out operation by using the water supply guiding surface formed on the elevator. Therefore, the above-described demand cannot be satisfied, and as a result, there is a problem in that operability is poor.

The present invention has been made in view of such circumstances, and an object of the present invention is to provide an endoscope capable of improving the operability of the endoscope.

In order to achieve the object of the present invention, an endoscope according to an aspect of the present invention comprises: a distal end portion main body that is provided on a distal end side of an insertion part; an elevator housing portion that is provided in the distal end portion main body and that is open in a first direction orthogonal to a longitudinal axis direction of the insertion part; an elevator that is rotatably provided in the elevator housing portion; an observation optical system that is disposed on a wall portion of the distal end portion main body adjacent to the elevator housing portion and that observes a visual field region in the first direction in which the elevator housing portion is open; an outflow port that is provided in the distal end portion main body and through which liquid flows out; and a cap that is attachably and detachably attached to the distal end portion main body and that has a liquid guiding surface that guides the liquid flowing out from the outflow port in a direction toward the visual field region.

In the aspect of the present invention, it is preferable that the cap has an inflow portion facing the outflow port in a state where the cap is attached to the distal end portion main body, a jetting portion that is open toward the visual field region, and a flow path connecting the inflow portion and the jetting portion to each other, and that a wall surface of the flow path is formed as the liquid guiding surface.

In the aspect of the present invention, it is preferable that the jetting portion is configured such that a jetting direction is directed to a position separated from the observation optical system in an optical axis direction of the observation optical system.

In the aspect of the present invention, it is preferable that a position of the jetting portion in the longitudinal axis direction is located on a base end side in the longitudinal axis direction with respect to a position of the observation optical system in the longitudinal axis direction.

In the aspect of the present invention, it is preferable that a position of the jetting portion in the longitudinal axis direction is located on a distal end side in the longitudinal axis direction with respect to a position of the observation optical system in the longitudinal axis direction.

In the aspect of the present invention, it is preferable that the elevator housing portion and the observation optical system are disposed adjacent to each other in a second direction orthogonal to the longitudinal axis direction and orthogonal to the first direction, and that the jetting portion is disposed on a side opposite to the observation optical system with the elevator housing portion interposed therebetween.

In the aspect of the present invention, it is preferable that the elevator housing portion and the observation optical system are disposed adjacent to each other in a second direction orthogonal to the longitudinal axis direction and orthogonal to the first direction, and that the jetting portion is disposed on a side opposite to the elevator housing portion with the observation optical system interposed therebetween.

In the aspect of the present invention, it is preferable that the outflow port is configured such that an outflow direction is directed in a direction along the longitudinal axis direction.

In the aspect of the present invention, it is preferable that the outflow port is configured such that an outflow direction is directed in a direction along the second direction.

In the aspect of the present invention, it is preferable that the liquid guiding surface is formed by an inner wall surface of a groove formed in the cap.

In the aspect of the present invention, it is preferable that the liquid guiding surface is formed by an inner wall surface of a through-hole formed in the cap.

According to the present invention, it is possible to improve operability of the endoscope.

DESCRIPTION OF THE PREFERRED EMBODIMENTS

Hereinafter, preferred embodiments of an endoscope of the present invention will be described with reference to the accompanying drawings.

Figure 1:
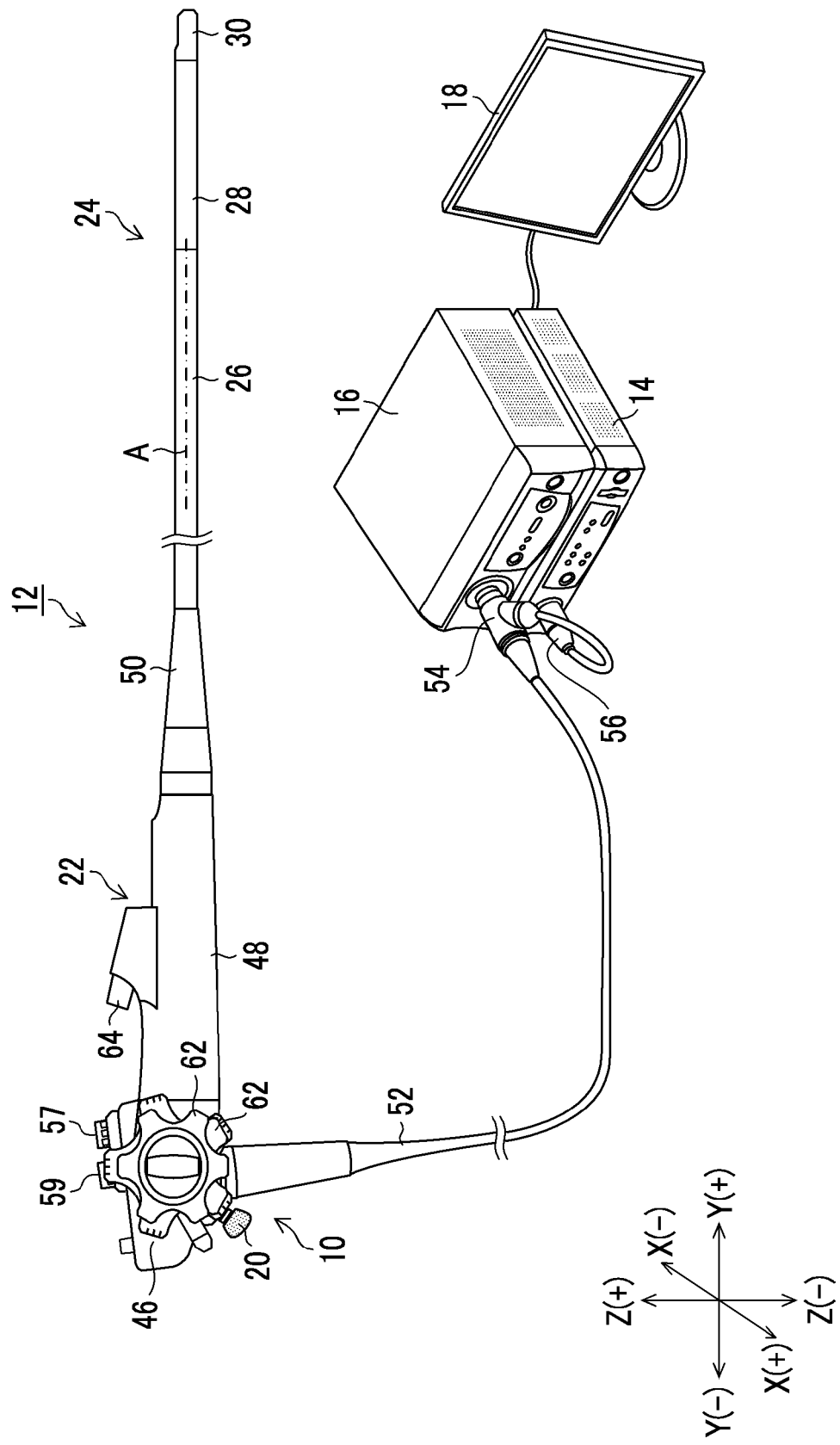
FIG. 1 is a configuration diagram of an endoscope system comprising an endoscope according to an embodiment.

FIG. 1 is a configuration diagram of an endoscope system 12 comprising an endoscope 10 according to an embodiment of the present invention. The endoscope system 12 comprises an endoscope 10, a processor device 14, a light source device 16, and a display 18.

The endoscope 10 comprises an operation part 22 provided with an elevating operation lever 20 and an insertion part 24 provided on a distal end side of the operation part 22 and inserted into a subject.

The insertion part 24 has a longitudinal axis A extending from a base end to a distal end, and comprises a flexible portion 26, a bending portion 28, and a distal end portion 30 in this order from the base end to the distal end. The detailed configuration of the distal end portion 30 will be described below, but first, a schematic configuration of the distal end portion 30 will be described.

Figure 2:
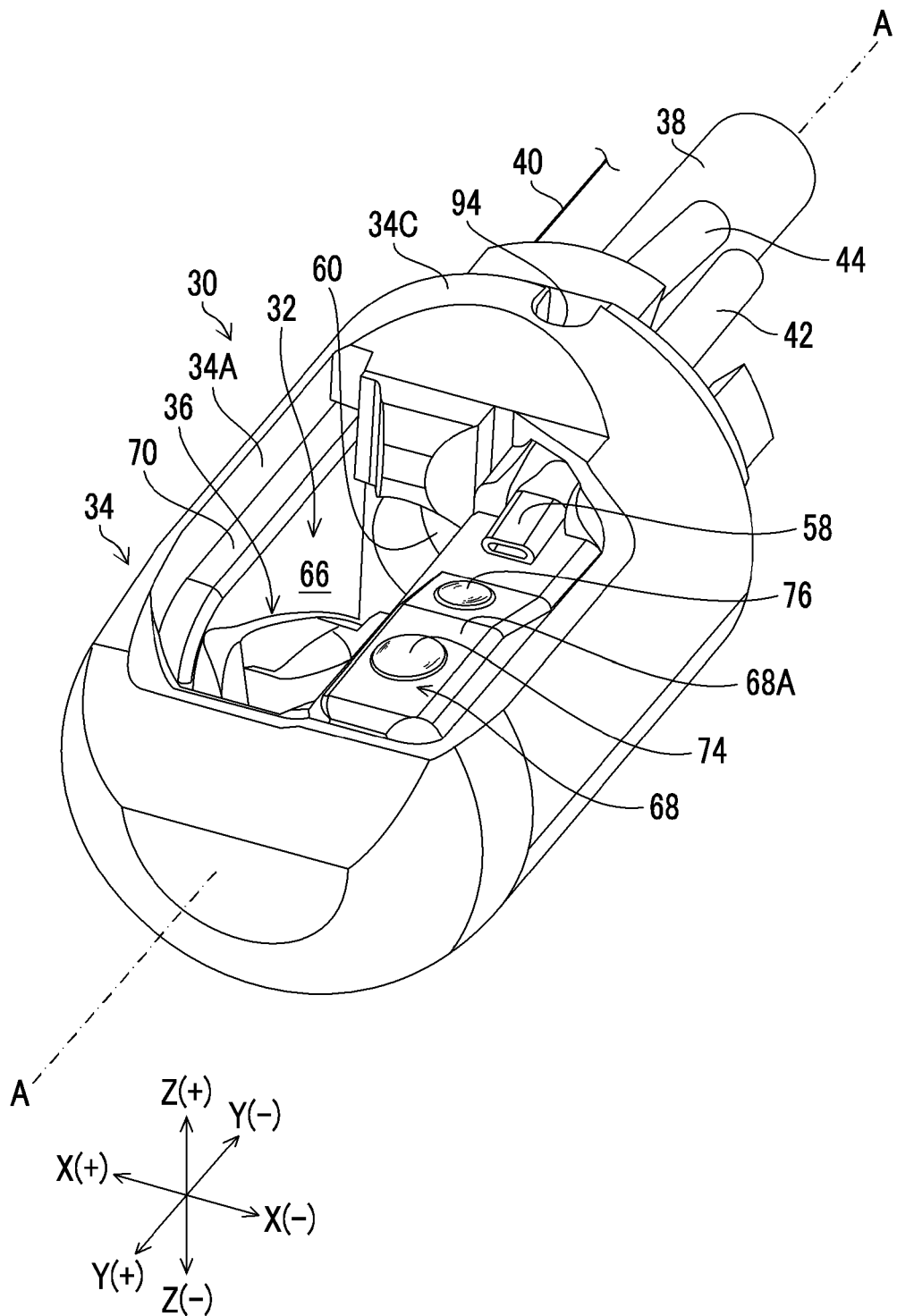
FIG. 2 is an enlarged perspective view of a distal end portion.

FIG. 2 is an enlarged perspective view of the distal end portion 30. Here, the endoscope 10 (see FIG. 1) of the embodiment is a side-viewing endoscope used as, for example, a duodenoscope, and the distal end portion 30 of FIG. 2 has a configuration in the side-viewing endoscope.

Figure 3:
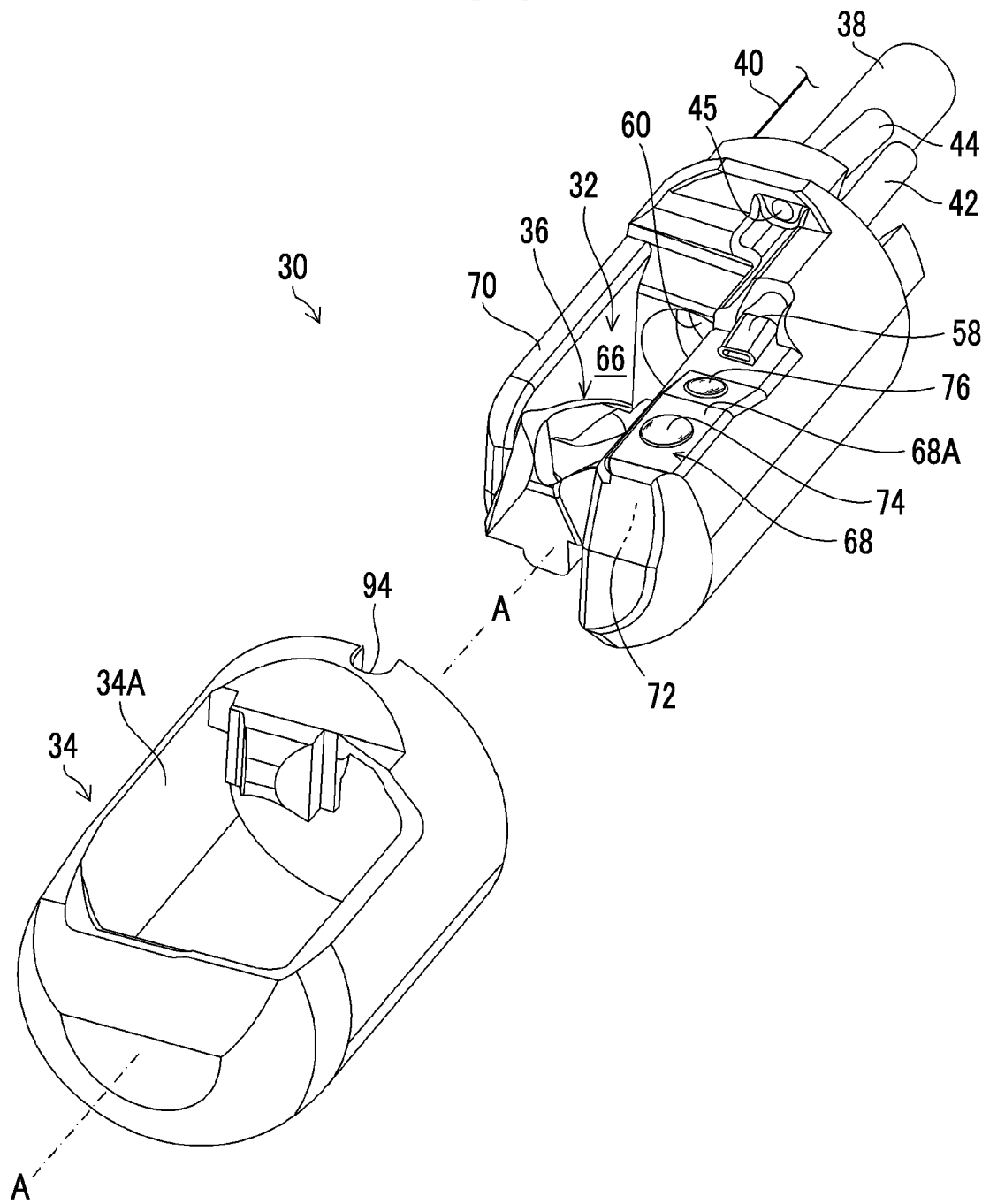
FIG. 3 is an assembly perspective view showing a configuration of the distal end portion shown in FIG. 2.

FIG. 3 is an assembly perspective view showing the configuration of the distal end portion 30 shown in FIG. 2. As shown in FIG. 3, the distal end portion 30 has a distal end portion main body 32 and a cap 34, and is configured by mounting the cap 34 on the distal end portion main body 32. The distal end portion main body 32 is provided on a distal end side of the insertion part 24 (see FIG. 1), and the distal end portion main body 32 is provided with an elevator 36, which will be described below. In FIGS. 2 and 3, a state in which the elevator 36 is located in a lying position is shown.

In addition, FIGS. 2 and 3 show various components disposed inside the insertion part 24 of the endoscope 10 (see FIG. 1). Specifically, a treatment tool channel 38 that guides a distal end portion of a treatment tool (not shown) to the distal end portion main body 32, an elevating operation wire 40 (hereinafter, referred to as a wire 40) for performing an operation of changing a lead-out direction of the distal end portion of the treatment tool that is led out from the distal end portion main body 32, an air and water supply tube 42, and a liquid supply tube 44 are provided. In addition, although not shown in FIGS. 2 and 3, components such as an angle wire for performing an operation of changing a bending direction of the bending portion 28 (see FIG. 1), a signal cable for transmitting an image signal, and a light guide for transmitting illumination light are also provided.

In the present specification, a configuration of each part will be described by using a three-dimensional orthogonal coordinate system including three-axis directions (X-axis direction, Y-axis direction, and Z-axis direction). For example, in FIGS. 1 to 3, a Z(+) direction indicates an upward direction and a Z(−) direction indicates a downward direction. In addition, an X(+) direction indicates a right direction and an X(−) direction indicates a left direction. Furthermore, a Y(+) direction indicates a direction toward the distal end of the distal end portion 30, and a Y(−) direction indicates a direction toward the base end side of the distal end portion 30. The Y-axis direction including the Y(+) direction and the Y(−) direction is parallel to the longitudinal axis A direction of the insertion part 24.

Returning to FIG. 1, the operation part 22 has a substantially cylindrical shape as a whole. The operation part 22 has an operation part main body 46 in which the elevating operation lever 20 is rotatably provided, and a grip portion 48 connected to the operation part main body 46, and a base end portion of the insertion part 24 is provided on the distal end side of the grip portion 48 through a bending-proof pipe 50. The grip portion 48 is a portion that is gripped by an operator during the operation of the endoscope 10.

The operation part main body 46 comprises a universal cable 52. A light source connector 54 is provided on the distal end side of the universal cable 52. The light source connector 54 is provided with an electric connector 56 branched. The electric connector 56 is connected to the processor device 14, and the light source connector 54 is connected to the light source device 16.

An air and water supply button 57 and a suction button 59 are provided on the operation part main body 46 side by side. In a case where the air and water supply button 57 is operated, air and liquid are supplied to the air and water supply tube 42 in FIG. 2, and air and liquid can be jetted from an air and water supply nozzle 58 provided in the distal end portion main body 32.

The liquid supply tube 44 is disposed in the universal cable 52 from the insertion part 24 through the operation part 22, and an opening at an end portion thereof is formed as a connector connection part (not shown) for water jet to the light source connector 54. A water tank (not shown) is connected to the connector connection part through a liquid supply pump (not shown). In a case where the liquid supply pump is driven by an electric switch provided separately, water is supplied from the water tank to the liquid supply tube 44 through the connector connection part. As shown in FIG. 3, the distal end of the liquid supply tube 44 is open as an outflow port 45 in the distal end portion main body 32. The liquid may be supplied to the liquid supply tube 44 by switching a liquid supply pipe line from the air and water supply tube 42 to the liquid supply tube 44 by fully pressing the air and water supply button 57.

In a case where the suction button 59 in FIG. 1 is operated, body fluid, such as blood, can be sucked through the treatment tool channel 38 from a suction port that also serves as a treatment tool lead-out port 60 provided in the distal end portion main body 32 in FIG. 2.

As shown in FIG. 1, a pair of angle knobs 62 and 62 that perform an operation of bending the bending portion 28 are disposed on the operation part main body 46. The pair of angle knobs 62 and 62 are coaxially provided so as to be rotationally movable.

The elevating operation lever 20 is rotatably provided coaxially with the angle knobs 62 and 62. The elevating operation lever 20 is rotationally operated by a hand of the operator who grips the grip portion 48. In a case where the elevating operation lever 20 is rotationally operated, the wire 40 in FIG. 2 is pushed and pulled in conjunction with the rotary operation of the elevating operation lever 20. By such an operation of the wire 40, the posture of the elevator 36 coupled to the distal end side of the wire 40 is changed between a lying position in FIG. 3 and an elevating position (not shown).

As shown in FIG. 1, the grip portion 48 of the operation part 22 is provided with a treatment tool lead-in port 64 to which the treatment tool is led in. The treatment tool (not shown) led in from the treatment tool lead-in port 64 with the distal end portion at the head is inserted into the treatment tool channel 38 in FIG. 2 and is led out to the outside from the treatment tool lead-out port 60 provided in the distal end portion main body 32.

As shown in FIG. 1, the flexible portion 26 of the insertion part 24 has a spiral pipe (not shown) formed by spirally winding a thin elastic strip-shaped plate made of metal. The flexible portion 26 is configured by covering the outside of the spiral pipe with a cylindrical net body braided using a metal wire and covering an outer peripheral surface of the net body with an outer sheath made of resin.

The bending portion 28 of the insertion part 24 has a structure in which a plurality of angle rings (not shown) are coupled to each other so as to be rotationally moved. The bending portion 28 is configured by covering the outer periphery of the structure with a cylindrical net body braided using a metal wire and covering the outer peripheral surface of the net body with a cylindrical outer sheath made of rubber. For example, four angle wires (not shown) are disposed from the bending portion 28 configured in this way to the angle knobs 62 and 62, and the bending portion 28 is bent upward, downward, leftward, and rightward by pushing and pulling these angle wires by the rotational operation of the angle knobs 62 and 62.

The endoscope 10 of the embodiment configured as described above is, as described above, a side-viewing endoscope used as a duodenoscope, and the insertion part 24 is inserted into a subject through the oral cavity. The insertion part 24 is inserted from the esophagus via the stomach to the duodenum, and a treatment, such as a predetermined test or a remedy, is performed.

Examples of the treatment tool used in the endoscope 10 of the embodiment include biopsy forceps having a cup capable of collecting a living tissue at a distal end portion thereof, an endoscopic sphincterotomy (EST) knife, or a contrast tube.

Next, the structure of the distal end portion 30 shown in FIGS. 2 and 3 will be described in detail.

The distal end portion 30 comprises the distal end portion main body 32 and the cap 34 that is attachably and detachably mounted on the distal end portion main body 32. The cap 34 is formed of a substantially cylindrical body whose distal end side is sealed and base end side is open, and an opening window 34A having a substantially rectangular shape is provided on a part of the outer peripheral surface thereof. In a case where the cap 34 is mounted on the distal end portion main body 32 as shown in FIG. 2, the opening window 34A is disposed in the Z(+) direction, which is a first direction orthogonal to the longitudinal axis A direction. Thus, the treatment tool lead-out port 60 of the distal end portion main body 32 communicates with the opening window 34A through an elevator housing portion 66. The elevator housing portion 66 will be described below.

The cap 34 is made of an elastic material, for example, a rubber material such as fluororubber or silicon rubber, or a resin material such as polysulfone or polycarbonate. A projecting engaging portion (not shown) to be engaged with a groove-shaped engaged portion (not shown) formed on the distal end portion main body 32 is provided on the base end side of the cap 34, and the engaging portion is engaged with the engaged portion, so that the cap 34 is mounted on the distal end portion main body 32. In a case where the treatment of the endoscope 10 is completed, the cap 34 is removed from the distal end portion main body 32 and is washed and disinfected, or is discarded as a disposable.

As shown in FIG. 3, the distal end portion main body 32 has a pair of wall portions 68 and 70 projecting toward the Y(+) side, and these wall portions 68 and 70 are disposed to face each other in the X-axis direction. In addition, the above-described elevator housing portion 66 that houses the elevator 36 is provided between the wall portion 68 and the wall portion 70. The elevator housing portion 66 is open in the Z(+) direction and the Z(−) direction, which are the first directions orthogonal to the longitudinal axis A direction.

With regard to a positional relationship between the wall portion 68 and the elevator housing portion 66, the wall portion 68 is disposed adjacent to the elevator housing portion 66 in the X direction. Further, an illumination optical system 74 having an illumination window and an observation optical system 76 having an observation window are disposed adjacent to each other in the Y direction on an upper surface 68A of the wall portion 68 on the Z(+) side. With this observation optical system 76, it is possible to observe the visual field region in the Z(+) direction in which the elevator housing portion 66 is open.

With regard to a positional relationship between the observation optical system 76 and the elevator housing portion 66, the observation optical system 76 and the elevator housing portion 66 are disposed adjacent to each other in the X direction, which is a second direction orthogonal to the longitudinal axis A direction and orthogonal to the Z(+) direction. The above-described air and water supply nozzle 58 is provided on the distal end portion main body 32 toward the observation optical system 76, whereby the observation optical system 76 is washed and dried by air and liquid jetted from the air and water supply nozzle 58.

A housing chamber 72 is provided inside the wall portion 68. An illumination unit (not shown) and an imaging unit (not shown) are housed in the housing chamber 72. The illumination unit comprises a light guide (not shown) disposed on the housing chamber 72 side of the illumination optical system 74. The light guide is disposed in the universal cable 52 from the insertion part 24 of the endoscope 10 (see FIG. 1) through the operation part 22, and a base end thereof is connected to the light source connector 54. Accordingly, in a case where the light source connector 54 is connected to the light source device 16, illumination light from the light source device 16 is emitted from the illumination optical system 74 toward the visual field region existing in the Z(+) direction through the light guide.

The above-described imaging unit comprises a complementary metal oxide semiconductor (CMOS) type or charge coupled device (CCD) type imaging element (not shown) disposed on the housing chamber 72 side of the observation optical system 76. A subject image is formed on an image forming surface of the imaging element by an image forming lens (not shown) constituting the observation optical system 76. A distal end of a signal cable (not shown) is connected to the imaging element, the signal cable is disposed in the universal cable 52 from the insertion part 24 of the endoscope 10 (see FIG. 1) through the operation part 22, and a base end thereof is connected to the electric connector 56. Accordingly, in a case where the electric connector 56 is connected to the processor device 14, an imaging signal of the subject image obtained by the observation optical system 76 is transmitted to the processor device 14 through the signal cable. Then, the imaging signal is subjected to image processing by the processor device 14, and then displayed on the display 18 as a subject image.

Figure 4:
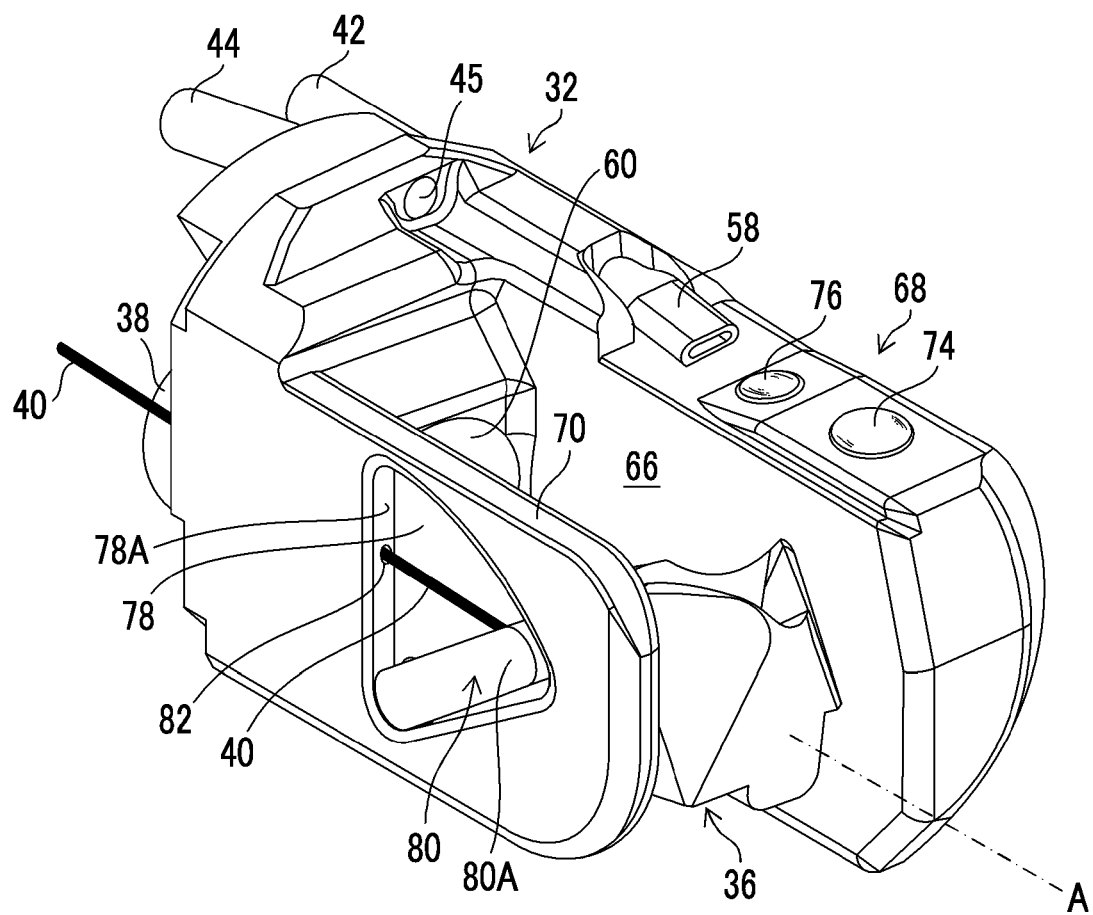
FIG. 4 is a perspective view of a distal end portion main body as viewed from an X(+) side.
Figure 4:
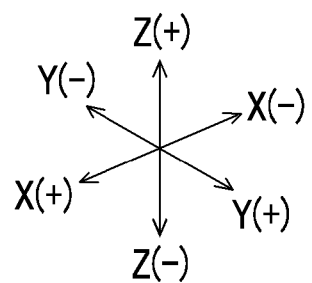

Next, the configuration of the elevator 36 will be described with reference to FIGS. 4 and 5. FIG. 4 is a perspective view of the distal end portion main body 32 of FIG. 3 as viewed from the X(+) side, and FIG. 5 is a perspective view showing assembly of the distal end portion main body 32 and the elevator 36.

An elevating lever housing chamber 78 is provided on a side surface of the wall portion 70 on the X(+) side, and an elevating lever 80 is housed in the elevating lever housing chamber 78. The elevating lever housing chamber 78 has a fan-shaped concave shape, is covered with a protective plate (not shown), and is sealed. In addition, a through-hole 82 for allowing the wire 40 to penetrate therethrough is provided on a side surface 78A of the elevating lever housing chamber 78 on the Y(−) side along the Y-axis direction. A distal end of the wire 40 is inserted into the through-hole 82 and is fixed to a lever portion 80A of the elevating lever 80.

Figure 5:
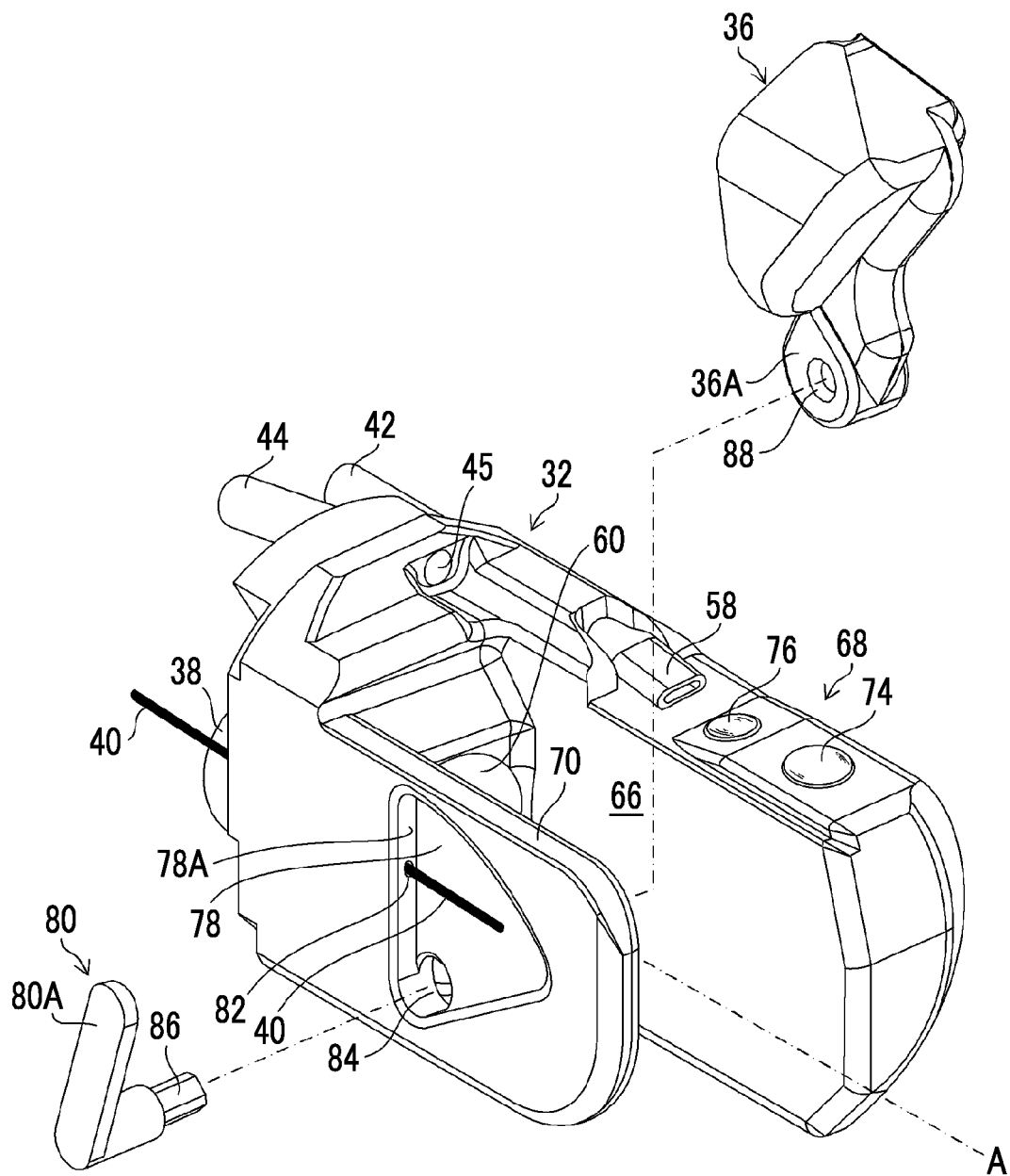
FIG. 5 is a perspective view showing assembly of a distal end portion main body and an elevator.
Figure 5:
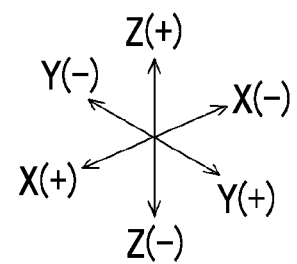

As shown in FIG. 5, the wall portion 70 comprises a through-hole 84 penetrating through the elevating lever housing chamber 78 and the elevator housing portion 66 along the X-axis direction. A rotary shaft 86 of the elevating lever 80 is disposed so as to penetrate through the through-hole 84 and is rotatably and pivotally supported. A distal end of the rotary shaft 86 is fitted into a hole 88 provided in a base portion 36A of the elevator 36. Thus, the elevating lever 80 and the elevator 36 are coupled to each other through the rotary shaft 86.

Therefore, according to the distal end portion main body 32 configured as described above, in a case where the wire 40 is pushed and pulled by the elevating operation lever 20 (see FIG. 1), the rotary shaft 86 rotates together with the elevating lever 80, whereby the posture of the elevator 36 is changed between the lying position and the elevating position (not shown). By this operation, the lead-out direction of the treatment tool led out from the treatment tool lead-out port 60 to the elevator housing portion 66 can be changed. An O-ring (not shown) is disposed between the rotary shaft 86 and the through-hole 84 to prevent gas and liquid from entering the elevator housing portion 66 and the elevating lever housing chamber 78.

Next, a liquid jetting device that jets liquid toward the visual field region of the observation optical system 76 will be described.

Figure 6:
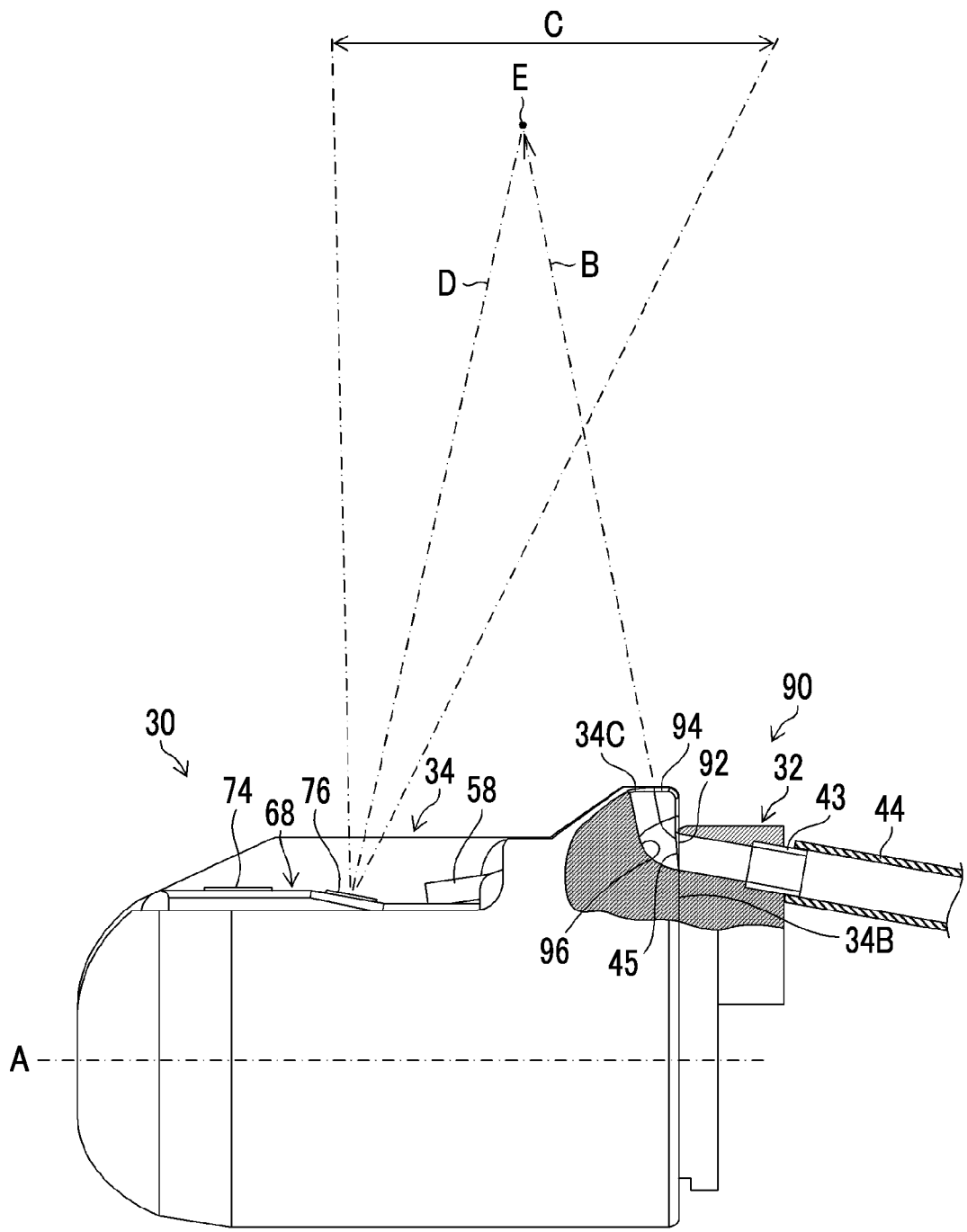
FIG. 6 is a cross-sectional view of a main part of a distal end portion showing a configuration of a liquid jetting device of a first embodiment.
Figure 6:
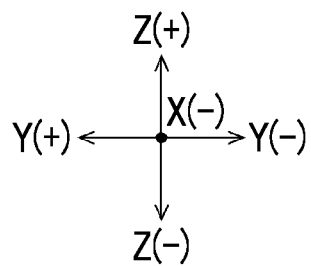
Figure 7:
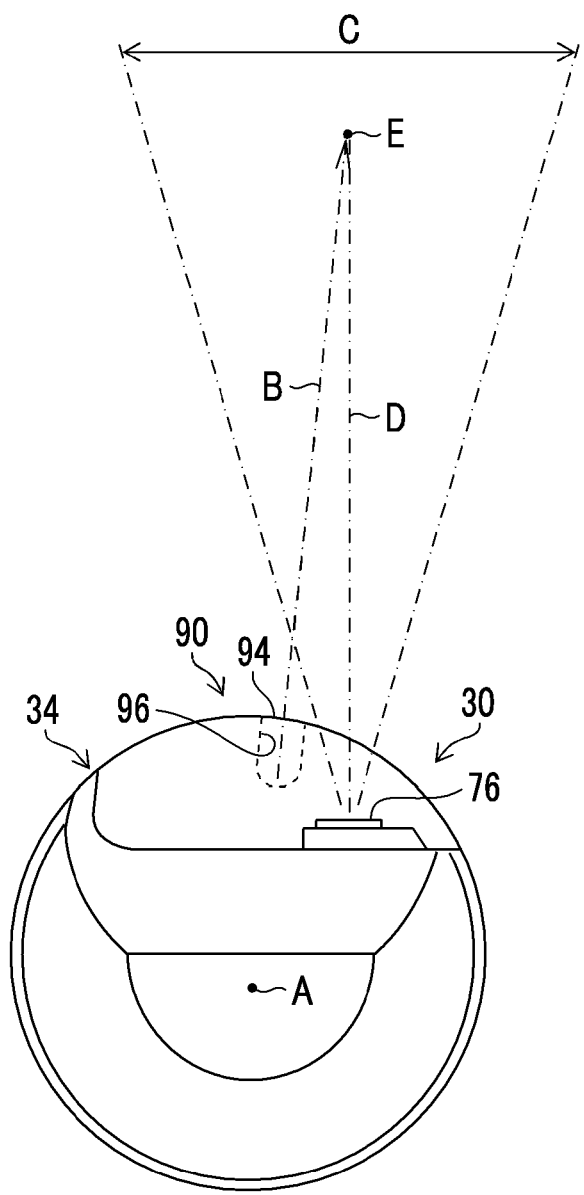
FIG. 7 is a front view of the distal end portion shown in FIG. 6 as viewed from a Y(+) side.
Figure 7:
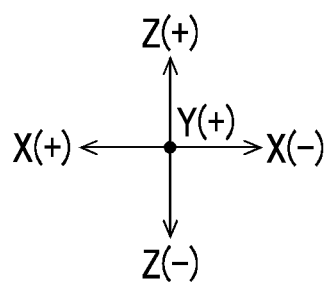

FIG. 6 is a cross-sectional view of the main part of the distal end portion 30 showing the configuration of a liquid jetting device 90 of a first embodiment, and is a cross-sectional view of the main part of the distal end portion 30 as viewed from the X(−) side. FIG. 7 is a front view of the distal end portion 30 shown in FIG. 6 as viewed from the Y(+) side, and FIG. 8 is a top view of the distal end portion 30 shown in FIG. 6 as viewed from the Z(+) side.

Figure 8:
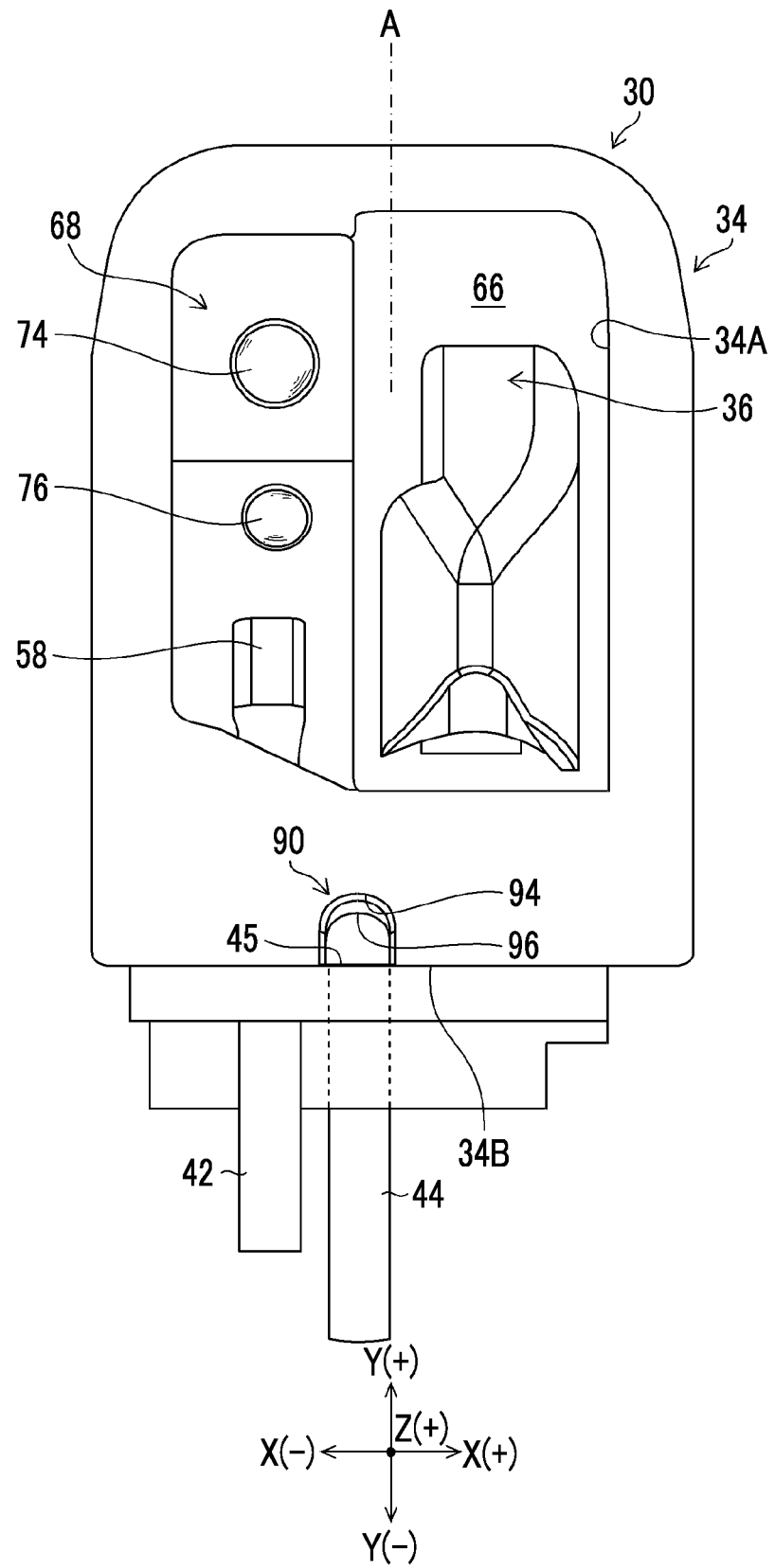
FIG. 8 is a top view of the distal end portion shown in FIG. 6 as viewed from a Z(+) side.

As shown in FIGS. 6 to 8, the liquid jetting device 90 of the first embodiment has: the liquid supply tube 44 having the outflow port 45 that is open at the distal end thereof; and an inflow portion 92, a jetting portion 94, and a bent flow path 96 provided in the cap 34. As shown in FIG. 6, a distal end of the liquid supply tube 44 is connected to the outflow port 45 of the distal end portion main body 32 through a joint pipe 43. In addition, the joint pipe 43 is adhered or screwed to the outflow port 45.

As an example, the outflow port 45 is configured in the distal end portion main body 32 such that an outflow direction is directed in a direction along the longitudinal axis A direction (see FIG. 3).

As shown in FIG. 6, the inflow portion 92 provided in the cap 34 is provided in an end surface 34B of the cap 34 on the Y(−) side. In addition, the inflow portion 92 is provided at a position facing the outflow port 45 in a state where the cap 34 is attached to the distal end portion main body 32.

The jetting portion 94 is provided on an upper surface 34C of the cap 34 on the Z(+) side. In addition, a position of the jetting portion 94 in the longitudinal axis A direction is located on the base end side in the longitudinal axis A direction with respect to a position of the observation optical system 76 in the longitudinal axis A direction. Further, the jetting portion 94 is open toward a visual field region C of the observation optical system 76 as shown by an arrow B indicated by a one-dot chain line in FIGS. 6 and 7.

The bent flow path 96 is bent toward the Z(+) side in the Y-axis direction from the inflow portion 92 toward the jetting portion 94. As an example, the bent flow path 96 is formed by a groove formed in the cap 34, and a wall surface of the bent flow path 96 is formed as a liquid guiding surface. That is, the liquid flowing out from the outflow port 45 is guided in a direction toward the visual field region by the wall surface of the bent flow path 96. In addition, according to the present embodiment in which the bent flow path 96 is formed of a groove, it is advantageous in a case where a thickness of a portion of the cap 34 where the bent flow path 96 is formed is not sufficient to form a through-hole.

Next, the operation of the liquid jetting device 90 of the first embodiment will be described.

By driving the liquid supply pump, the liquid supplied to the liquid supply tube 44 (see FIG. 3) flows into the inflow portion 92 from the outflow port 45 in FIG. 6. Then, the liquid is smoothly guided to the jetting portion 94 by passing through the bent flow path 96, and then is jetted from the jetting portion 94 toward the visual field region C as shown by the arrow B. Thus, the liquid can be supplied to an observation site located in the visual field region C. Since the cap 34 comprises the bent flow path 96 forming the liquid guiding surface, the liquid supply operation can be performed independently of the raising and lowering operation of the elevator 36 by the elevating operation lever 20 (see FIG. 1). Therefore, the raising and lowering operation of the elevator 36 and the liquid supply operation can be performed at the same time.

As described above, according to the endoscope 10 of the embodiment, since the distal end portion main body 32 is provided with the outflow port 45 through which the liquid flows out, and the cap 34 is provided with the bent flow path 96 forming the liquid guiding surface, the treatment using the treatment tool can be performed while the liquid is supplied to the observation site. In other words, the liquid can be jetted toward the observation site without interfering with the operation of the treatment tool. Thus, for example, a bleeding part can be specified while washing it with liquid, and hemostasis can be performed using a treatment tool. In addition, endoscopic retrograde cholangiopancreatography can be performed using a treatment tool while washing away bile or fine gallstones with liquid.

In the embodiment, although the liquid guiding surface is formed by the bent flow path 96, the liquid guiding surface is not limited thereto, and may be formed of, for example, a linearly inclined flow path.

In addition, in the embodiment, although the outflow port 45 is configured such that the outflow direction is directed in the direction along the longitudinal axis A direction, this configuration is not necessarily limited thereto, and the outflow port 45 may be configured such that the outflow direction is directed to the Z(+) side, the X(+) side, or the X(−) side, for example. However, according to the configuration of the outflow port 45 of the embodiment, in a case of the washing of the liquid supply tube 44 using washing liquid, which is performed by removing the cap 34 from the distal end portion main body 32, the washing liquid can be made to flow out from the outflow port 45 toward the Y(+) side. That is, it is possible to prevent the washing liquid from splashing to the surroundings.

Although the jetting portion 94 is open toward the visual field region C of the observation optical system 76, it is more preferable that the jetting portion 94 is configured such that the jetting direction is directed to a position E separated from an outer surface of the observation optical system 76 in an optical axis D direction of the observation optical system 76. By configuring the jetting portion 94 in this way, the liquid jetted from the jetting portion 94 can be reliably jetted to the position E separated from the observation optical system 76 in the optical axis D direction. In addition, the position E is more preferably a position corresponding to a focal point of the observation optical system 76. Thus, a clear image of the observation site can be ensured.

Further, according to the liquid jetting device 90 of the first embodiment, as shown in FIG. 8, the position of the jetting portion 94 in the longitudinal axis A direction is located on the base end side in the longitudinal axis A direction with respect to the position of the observation optical system 76 in the longitudinal axis A direction. Therefore, the liquid jetting device 90 of the first embodiment can obtain the following effects.

Figure 9:
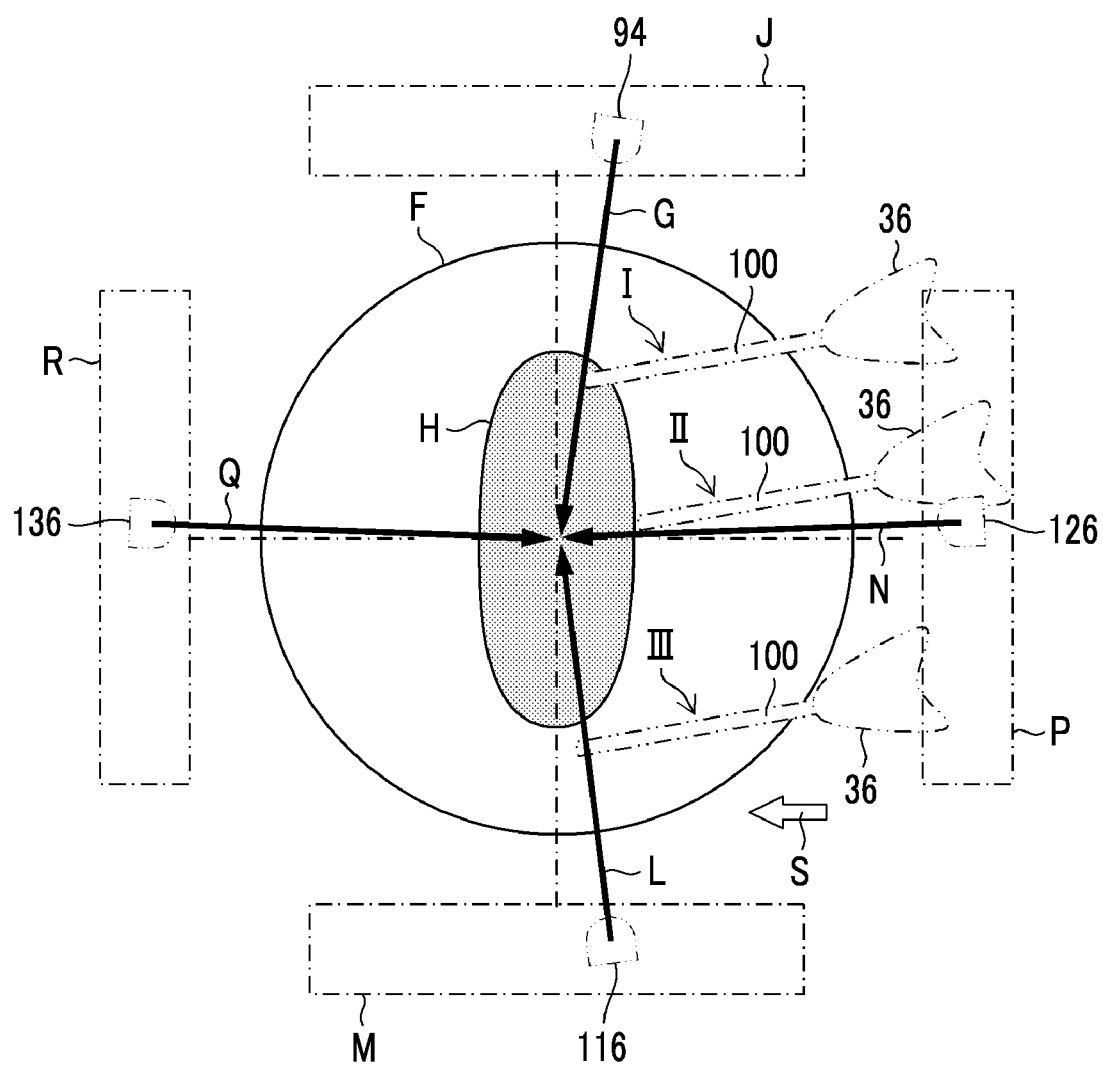
FIG. 9 is an explanatory view showing an image of a visual field region displayed on a display.

That is, FIG. 9 shows an image F of the visual field region C (see FIGS. 6 and 7) displayed on the display 18 (see FIG. 1). Since the jetting portion 94 is disposed at the position shown in FIG. 8, the liquid jetted from the jetting portion 94 is jetted from an upper side of the image F toward an observation site H located at a center part of the image F, as shown by a thick arrow G in FIG. 9 on the image F.

In FIG. 9, the elevator 36 and a treatment tool 100 are each shown by a two-dot chain line. The elevator 36 is not displayed on the image F, but is located on a right side of the image F. Then, the treatment tool 100 whose lead-out direction is changed by the raising and lowering operation of the elevator 36 is displayed on a right upper part of the image F indicated by reference numeral I in a case where the elevator 36 is located in the elevating position, is displayed on a right center part of the image F indicated by reference numeral II in a case where the elevator 36 is located between the elevating position and the lying position, and is displayed on a right lower part of the image F indicated by reference numeral III in a case where the elevator 36 is located in the lying position.

Therefore, according to the liquid jetting device 90 of the first embodiment, the treatment tool 100 appearing on the right side of the image F can be guided to a target position of the observation site H by the elevator 36 while liquid is supplied from the upper side of the image F toward the observation site H of the image F.

Although the jetting portion 94 shown in FIG. 8 is disposed substantially at the center of the cap 34 in the X-axis direction, the jetting portion 94 may be disposed in a position deviated in the X-axis direction from the position shown in FIG. 8 because the position of the jetting portion 94 need only be a position on the base end side in the longitudinal axis A direction with respect to the position of the observation optical system 76 in the longitudinal axis A direction. In this case, the jetting portion 94 is located in an optional position in a region J, which is formed on the upper side of the image F in FIG. 9 and is surrounded by a two-dot chain line, and the liquid can be jetted from the position to the observation site H.

Figure 10:
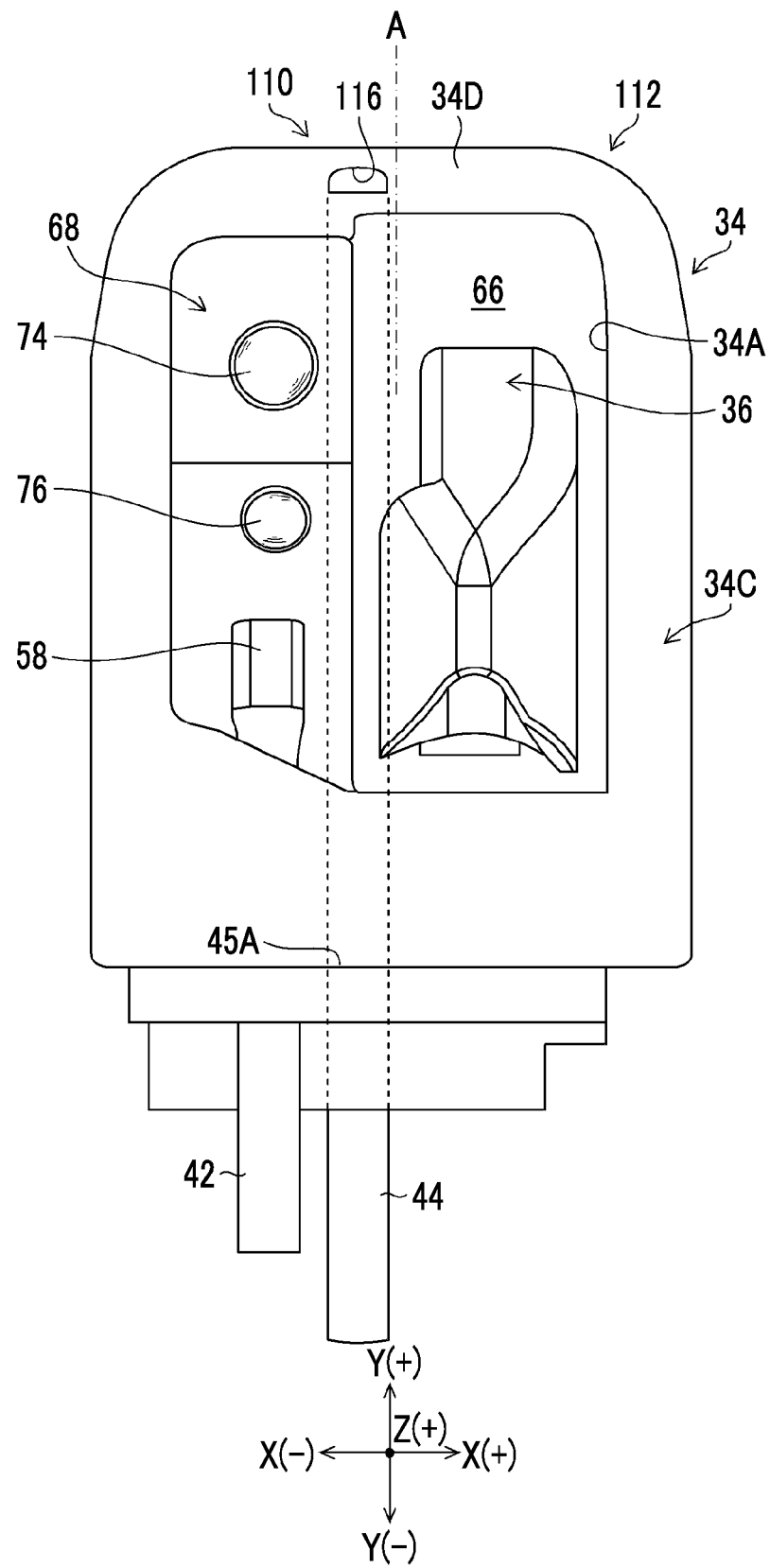
FIG. 10 is a top view of a distal end portion having a liquid jetting device of a second embodiment.
Figure 11:
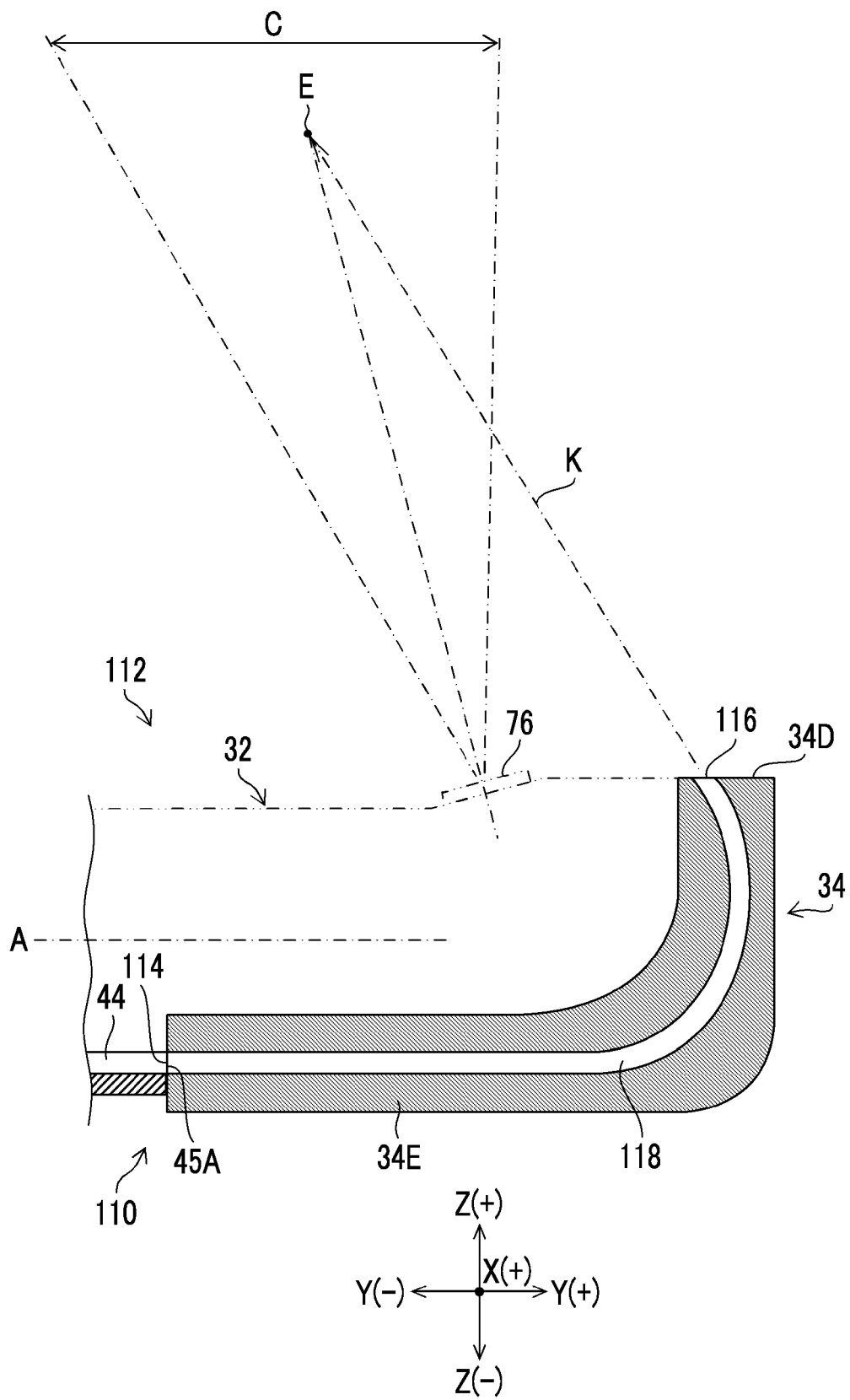
FIG. 11 is a schematic cross-sectional view of the distal end portion shown in FIG. 10 as viewed from an X(+) side.

FIG. 10 is a top view of a distal end portion 112 having a liquid jetting device 110 of a second embodiment, and is a top view as viewed from the Z(+) side. FIG. 11 is a schematic cross-sectional view of the distal end portion 112 of FIG. 10 as viewed from the X(+) side. In the description of the liquid jetting device 110 of the second embodiment, the same or similar members as those of the liquid jetting device 90 of the first embodiment shown in FIGS. 6 to 8 will be denoted by the same reference numerals.

As shown in FIGS. 10 to 11, the liquid jetting device 110 of the second embodiment has: the liquid supply tube 44 having an outflow port 45A that is open at a distal end thereof; and an inflow portion 114, a jetting portion 116, and a bent flow path 118 provided in the cap 34.

The outflow port 45A is disposed on the Z(−) side of the distal end portion main body 32 with respect to the outflow port 45 shown in FIG. 6. In addition, as shown in FIG. 11, the outflow port 45A is configured such that the outflow direction is directed in the direction along the longitudinal axis A direction.

The inflow portion 114 provided in the cap 34 is provided at a position facing the outflow port 45A in a state where the cap 34 is attached to the distal end portion main body 32.

As shown in FIG. 10, the jetting portion 116 is provided on a distal end upper surface 34D provided on the Y(+) side of the upper surface 34C of the cap 34. That is, a position of the jetting portion 116 in the longitudinal axis A direction is located on the distal end side in the longitudinal axis A direction with respect to a position of the observation optical system 76 in the longitudinal axis A direction. In addition, the jetting portion 116 is open toward the visual field region C of the observation optical system 76 as shown by an arrow K indicated by a one-dot chain line in FIG. 11.

The bent flow path 118 extends to the Y(+) side in the Y-axis direction from the inflow portion 114 toward the jetting portion 116, and then is bent toward the Z(+) side.

Next, the operation of the liquid jetting device 110 of the second embodiment will be described.

The liquid supplied to the liquid supply tube 44 of FIG. 11 flows into the inflow portion 114 from the outflow port 45A. Then, the liquid is smoothly guided to the jetting portion 116 by passing through the bent flow path 118, and then is jetted from the jetting portion 116 toward the visual field region C as shown by the arrow K. Thus, the liquid can be supplied to an observation site located in the visual field region C. According to the liquid jetting device 110, since the cap 34 comprises the inflow portion 114, the jetting portion 116, and the bent flow path 118, the liquid supply operation can be performed independently of the raising and lowering operation of the elevator 36 by the elevating operation lever 20 (see FIG. 1).

Therefore, in the liquid jetting device 110 of the second embodiment as well as the liquid jetting device 90 of the first embodiment, the treatment using the treatment tool can be performed while the liquid is supplied to the observation site.

Further, according to the liquid jetting device 110 of the second embodiment, as shown in FIG. 10, the position of the jetting portion 116 in the longitudinal axis A direction is located on the distal end side in the longitudinal axis A direction with respect to the position of the observation optical system 76 in the longitudinal axis A direction. Therefore, the liquid jetting device 110 of the second embodiment can obtain the following effects.

That is, the liquid jetted from the jetting portion 116 is jetted from a lower side of the image F toward the observation site H located at the center part of the image F, as shown by a thick arrow L on the image F in FIG. 9.

Therefore, according to the liquid jetting device 110 of the second embodiment, the treatment tool 100 appearing on the right side of the image F can be guided to a target position of the observation site H by the elevator 36 while the liquid is supplied from the lower side of the image F toward the observation site H of the image F.

Although the jetting portion 116 shown in FIG. 10 is disposed substantially at the center of the cap 34 in the X-axis direction, the jetting portion 116 may be disposed in a position deviated in the X-axis direction from the position shown in FIG. 10 because the position of the jetting portion 116 need only be a position on the distal end side in the longitudinal axis A direction with respect to the position of the observation optical system 76 in the longitudinal axis A direction. In this case, the jetting portion 116 is located in an optional position in a region M, which is formed on the lower side of the image F in FIG. 9 and is surrounded by a two-dot chain line, and the liquid can be jetted from the position to the observation site H.

Figure 12:
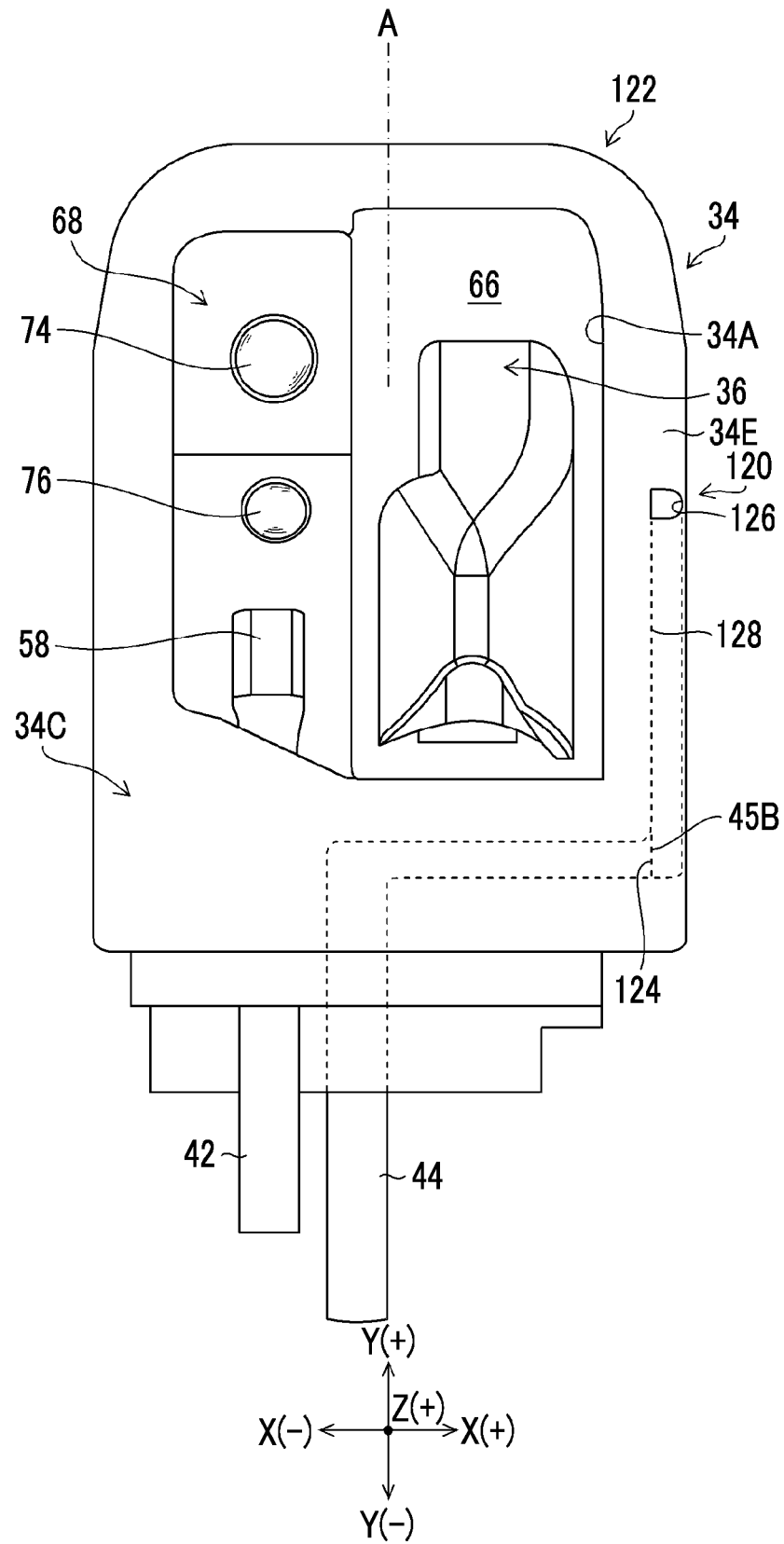
FIG. 12 is a top view of a distal end portion having a liquid jetting device of a third embodiment.

FIG. 12 is a top view of a distal end portion 122 having a liquid jetting device 120 of a third embodiment, and is a top view as viewed from the Z(+) side. In the description of the liquid jetting device 120 of the third embodiment, the same or similar members as those of the liquid jetting device 90 of the first embodiment shown in FIGS. 6 to 8 will be denoted by the same reference numerals.

As shown in FIG. 12, the liquid jetting device 120 has: the liquid supply tube 44 having an outflow port 45B that is open at a distal end thereof; and an inflow portion 124, a jetting portion 126, and a bent flow path 128 provided in the cap 34.

The outflow port 45B is disposed on a side surface of the distal end portion main body 32 on the X(+) side, and is configured such that the outflow direction is directed toward a direction on the X(+) side.

The inflow portion 124 provided in the cap 34 is provided at a position facing the outflow port 45B in a state where the cap 34 is attached to the distal end portion main body 32.

The jetting portion 126 is provided on a right upper surface 34E provided on the X(+) side of the upper surface 34C on the Z(+) side of the cap 34. That is, the jetting portion 126 is disposed on a side opposite to the observation optical system 76 with the elevator housing portion 66 interposed therebetween. The jetting portion 126 is also open toward the visual field region C (see FIGS. 6 and 7) of the observation optical system 76.

Although the detailed configuration of the bent flow path 128 is omitted, the bent flow path 128 extends to the Y(+) side in the Y-axis direction from the inflow portion 124 toward the jetting portion 126, and then is bent toward the Z(+) side.

Next, the operation of the liquid jetting device 120 will be described.

The liquid supplied to the liquid supply tube 44 flows into the inflow portion 124 from the outflow port 45B in FIG. 12. Then, the liquid is smoothly guided to the jetting portion 126 by passing through the bent flow path 128, and then is jetted from the jetting portion 126 toward the visual field region C. Thus, the liquid can be supplied to an observation site located in the visual field region C. According to the liquid jetting device 120, since the cap 34 comprises the inflow portion 124, the jetting portion 126, and the bent flow path 128, the liquid supply operation can be performed independently of the raising and lowering operation of the elevator 36 by the elevating operation lever 20 (see FIG. 1).

Therefore, in the liquid jetting device 120 of the third embodiment as well as the liquid jetting device 90 of the first embodiment, the treatment using the treatment tool can be performed while the liquid is supplied to the observation site.

Further, according to the liquid jetting device 120 of the third embodiment, the jetting portion 126 is disposed on the side opposite to the observation optical system 76 with the elevator housing portion 66 interposed therebetween. By disposing the jetting portion 126 in such a position, the liquid jetting device 120 of the third embodiment can obtain the following effects.

That is, the liquid jetted from the jetting portion 126 is jetted from a right side of the image F toward the observation site H located at the center part of the image F, as shown by a thick arrow N on the image F in FIG. 9.

Therefore, according to the liquid jetting device 120 of the third embodiment, the treatment tool 100 appearing on the right side of the image F can be guided to a target position of the observation site H by the elevator 36 while the liquid is supplied from the right side of the image F toward the observation site H of the image F.

Although the jetting portion 126 shown in FIG. 12 is disposed in the same position as the observation optical system 76 in the Y-axis direction, the jetting portion 126 may be disposed in a position deviated in the Y-axis direction (longitudinal axis A direction) from the position shown in FIG. 12 because the jetting portion 126 need only be disposed on the side opposite to the observation optical system 76 with the elevator housing portion 66 interposed therebetween. In this case, the jetting portion 126 is located in an optional position in a region P, which is formed on the right side of the image F in FIG. 9 and is surrounded by a two-dot chain line, and the liquid can be jetted from the position to the observation site H.

Figure 13:
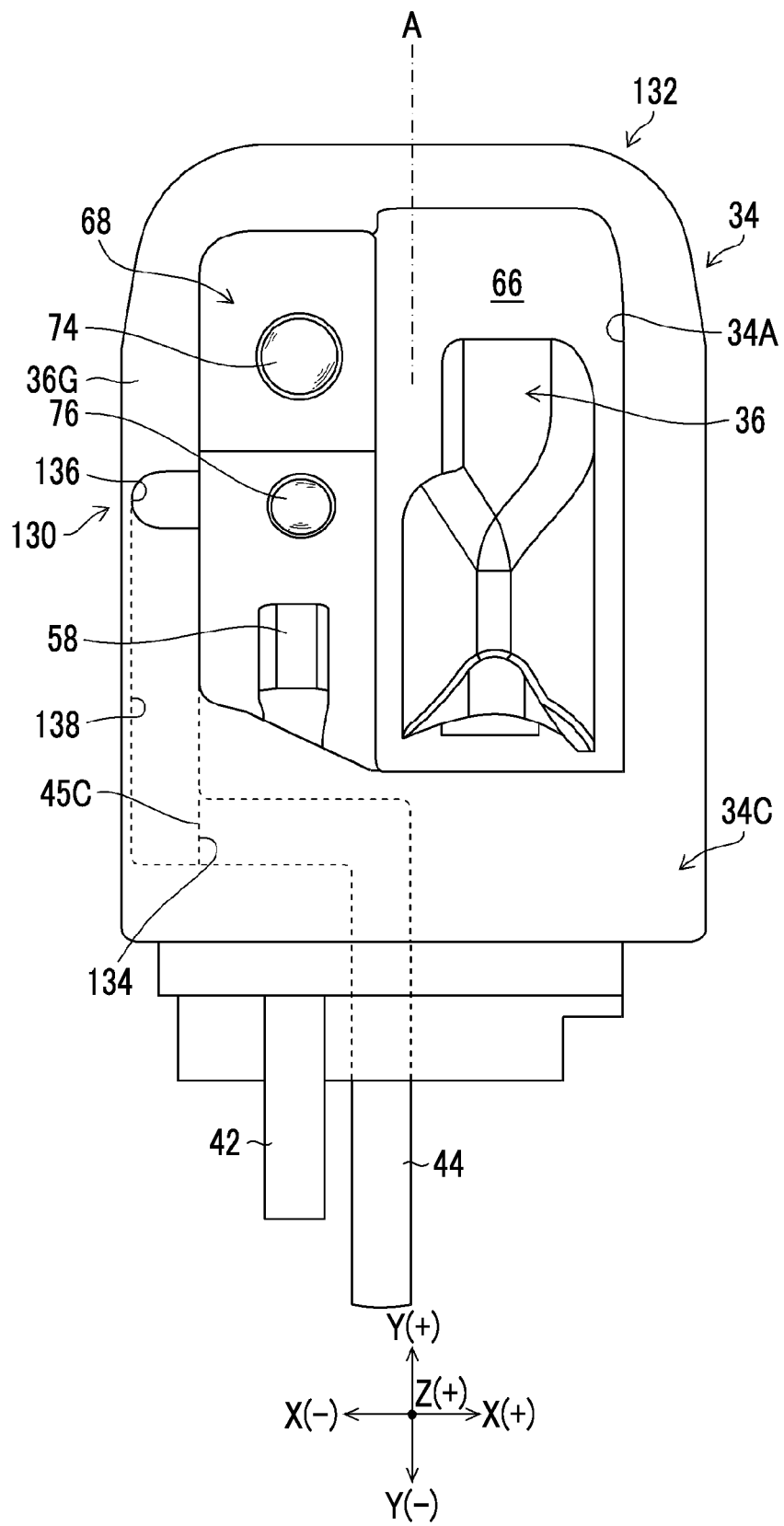
FIG. 13 is a top view of a distal end portion having a liquid jetting device of a fourth embodiment.
Figure 14:
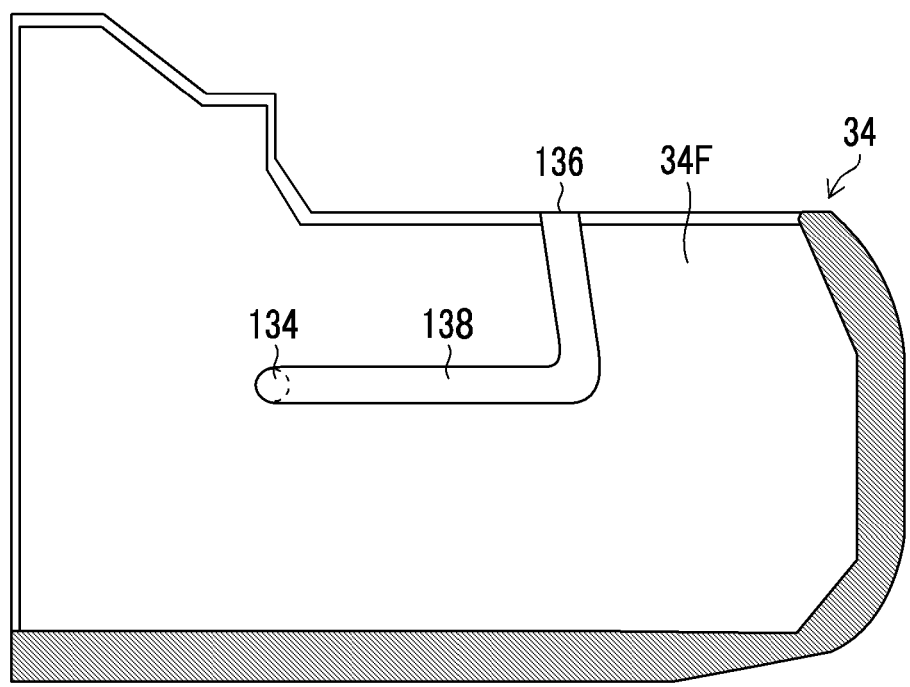
FIG. 14 is a side view of a left inner wall surface of a cap shown in FIG. 13 as viewed from an X(+) side.
Figure 14:
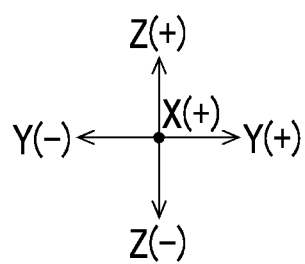

FIG. 13 is a top view of a distal end portion 132 having a liquid jetting device 130 of a fourth embodiment, and is a top view as viewed from the Z(+) side. In addition, FIG. 14 is a side view of a left inner wall surface 34F of the cap 34 as viewed from the X(+) side. In the description of the liquid jetting device 130 of the fourth embodiment, the same or similar members as those of the liquid jetting device 90 of the first embodiment shown in FIGS. 6 to 8 will be denoted by the same reference numerals.

As shown in FIG. 13, the liquid jetting device 130 has: the liquid supply tube 44 having an outflow port 45C that is open at a distal end thereof; and an inflow portion 134, a jetting portion 136, and a bent flow path 138 provided in the cap 34.

The outflow port 45C is disposed on a side surface of the distal end portion main body 32 on the X(−) side, and is configured such that the outflow direction is directed toward a direction on the X(−) side.

The inflow portion 134 provided in the cap 34 is provided at a position facing the outflow port 45C in a state where the cap 34 is attached to the distal end portion main body 32.

The jetting portion 136 is provided on a left upper surface 34G provided on the X(−) side of the upper surface 34C on the Z(−) side of the cap 34. That is, the jetting portion 136 is disposed on a side opposite to the elevator housing portion 66 with the observation optical system 76 interposed therebetween. The jetting portion 136 is also open toward the visual field region C (see FIGS. 6 and 7) of the observation optical system 76.

As shown in FIG. 14, the bent flow path 138 is formed as a groove formed on the left inner wall surface 34F. The bent flow path 138 extends to the Y(+) side in the Y-axis direction from the inflow portion 134 toward the jetting portion 136, and then is bent toward the Z(+) side. The bent flow path 138 may be formed as a through-hole.

Next, the operation of the liquid jetting device 130 will be described.

The liquid supplied to the liquid supply tube 44 of FIG. 13 flows into the inflow portion 134 from the outflow port 45C. Then, the liquid is smoothly guided to the jetting portion 136 by passing through the bent flow path 138, and then is jetted from the jetting portion 136 toward the visual field region C. Thus, the liquid can be supplied to an observation site located in the visual field region C. According to the liquid jetting device 130, since the cap 34 comprises the inflow portion 134, the jetting portion 136, and the bent flow path 138, the liquid supply operation can be performed independently of the raising and lowering operation of the elevator 36 by the elevating operation lever 20 (see FIG. 1).

Therefore, in the liquid jetting device 130 of the fourth embodiment as well as the liquid jetting device 90 of the first embodiment, the treatment using the treatment tool can be performed while the liquid is supplied to the observation site.

Further, according to the liquid jetting device 130 of the fourth embodiment, as shown in FIG. 13, the jetting portion 136 is disposed on the side opposite to the elevator housing portion 66 with the observation optical system 76 interposed therebetween. By disposing the jetting portion 136 in such a position, the liquid jetting device 130 of the fourth embodiment can obtain the following effects.

That is, the liquid jetted from the jetting portion 136 is jetted from a left side of the image F toward the observation site H located at the center part of the image F, as shown by a thick arrow Q on the image F in FIG. 9.

Therefore, according to the liquid jetting device 130 of the fourth embodiment, the treatment tool 100 appearing on the right side of the image F can be guided to a target position of the observation site H by the elevator 36 while the liquid is supplied from the left side of the image F toward the observation site H of the image F.

Although the jetting portion 136 shown in FIG. 13 is disposed in the same position as the observation optical system 76 in the Y-axis direction, the jetting portion 136 may be disposed in a position deviated in the Y-axis direction (longitudinal axis A direction) from the position shown in FIG. 13 because the jetting portion 136 need only be disposed on the side opposite to the elevator housing portion 66 with the observation optical system 76 interposed therebetween. In this case, the jetting portion 136 is located in an optional position in a region R, which is formed on the left side of the image F in FIG. 9 and is surrounded by a two-dot chain line, and the liquid can be jetted from the position to the observation site H.

In addition, according to the liquid jetting device 130 of the fourth embodiment, the liquid jetting direction (see arrow Q) can be opposed to the lead-out direction of the treatment tool 100 shown by an arrow S in FIG. 9. Therefore, there is an advantage in that the treatment tool 100 can be easily seen in comparison with the liquid jetting device 120 of the third embodiment in which the lead-out direction of the treatment tool 100 and the liquid jetting direction are the same on the image F.

<Other Inventions>

Figure 15:
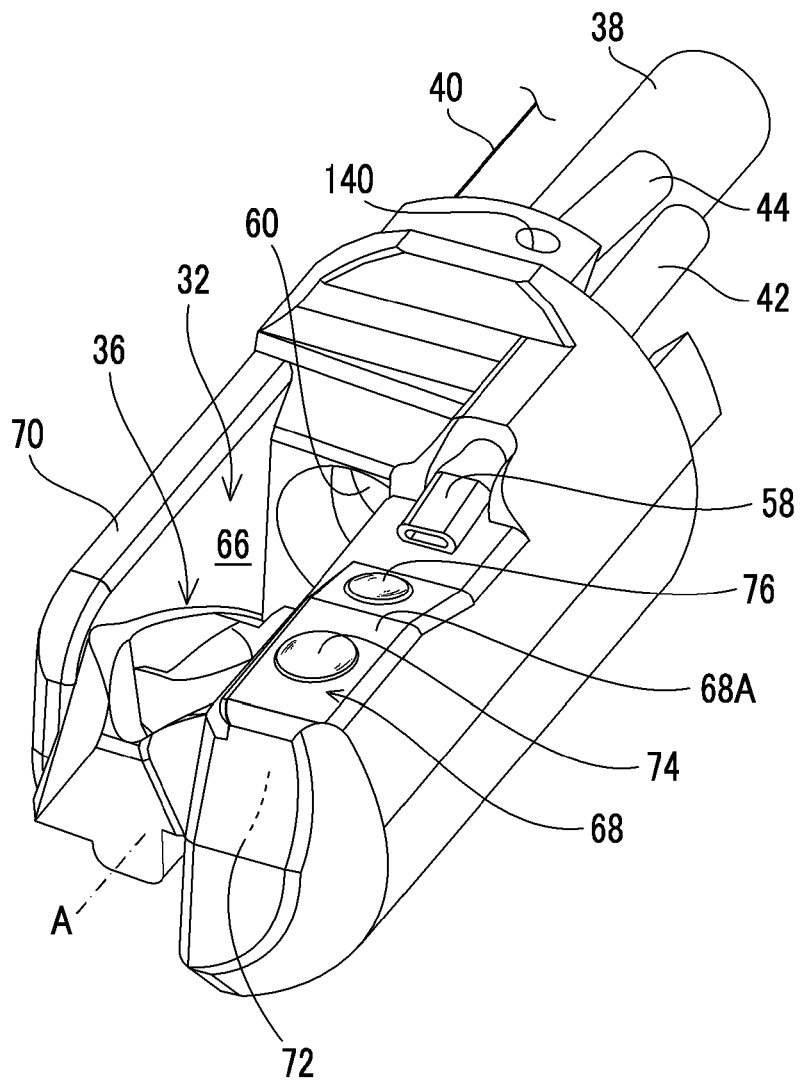
FIG. 15 is a perspective view of a distal end portion main body comprising a liquid jetting portion.

In the present invention, the liquid flowing out from the outflow port of the distal end portion main body is jetted into the visual field region by the liquid guiding surface provided in the cap. However, as another invention, as in the distal end portion main body 32 shown in FIG. 15, the distal end portion main body 32 may comprise a jetting portion 140 communicating with the liquid supply tube 44. The distal end portion main body 32 comprises a fluid guiding surface that guides the liquid in the direction toward the visual field region between the jetting portion 140 and the liquid supply tube 44. In addition, the jetting portion 140 is open toward the visual field region. Therefore, the liquid can be jetted from the jetting portion 140 of the distal end portion main body 32 into the visual field region. A position of the jetting portion 140 need only be disposed in a position exposed to the outside in a case where the cap 34 is mounted on the distal end portion main body 32, and may be provided on the upper surface 68A of the wall portion 68, for example. In addition, in a case of the configuration of the distal end portion main body which does not use the cap, the jetting portion need only be disposed in an optional position.

Although the present invention has been hitherto described, the present invention is not limited to the abovementioned examples, and various improvements and modifications may be made without departing from the scope of the present invention.

EXPLANATION OF REFERENCES

10: endoscope
12: endoscope system
14: processor device
16: light source device
18: display
20: elevating operation lever
22: operation part
24: insertion part
26: flexible portion
28: bending portion
30: distal end portion
32: distal end portion main body
34: cap
34A: opening window
34B: end surface
34C: upper surface
34D: distal end upper surface
34E: right upper surface
34F: left inner wall surface
36: elevator
36A: base portion
38: treatment tool channel
40: elevating operation wire
42: air and water supply tube
43: joint pipe
44: liquid supply tube
45: outflow port
45A: outflow port
45B: outflow port
45C: outflow port
46: operation part main body
48: grip portion
50: bending-proof pipe
52: universal cable
54: light source connector
56: electric connector
57: air and water supply button
58: air and water supply nozzle
59: suction button
60: treatment tool lead-out port
62: angle knob
64: treatment tool lead-in port
66: elevator housing portion
68: wall portion
68A: upper surface
70: wall portion
72: housing chamber
74: illumination optical system
76: observation optical system
78: elevating lever housing chamber
78A: side surface
80: elevating lever
80A: lever portion
82: through-hole
84: through-hole
86: rotary shaft
88: hole
90: liquid jetting device of first embodiment
92: inflow portion
94: jetting portion
96: bent flow path
100: treatment tool
110: liquid jetting device of second embodiment
112: distal end portion
114: inflow portion
116: jetting portion
118: bent flow path
120: liquid jetting device of third embodiment
122: distal end portion
124: inflow portion
126: jetting portion
128: bent flow path
130: liquid jetting device of fourth embodiment
132: distal end portion
134: inflow portion
136: jetting portion
138: bent flow path
140: jetting portion
A: longitudinal axis
C: visual field region
D: optical axis
E: position
F: image
H: observation site
J: region
M: region
P: region
R: region

What is claimed is:

1. An endoscope comprising:
a distal end portion main body that is provided on a distal end side of an insertion part;
an elevator housing portion that is provided in the distal end portion main body and is open in a first direction orthogonal to a longitudinal axis direction of the insertion part;
an elevator that is rotatably provided in the elevator housing portion;
an observation optical system that is disposed on a wall portion of the distal end portion main body adjacent to the elevator housing portion and that observes a visual field region in the first direction in which the elevator housing portion is open;
an outflow port that is provided in the distal end portion main body and through which liquid flows out; and
a cap that is attachably and detachably attached to the distal end portion main body and that has a liquid guiding surface that guides the liquid flowing out from the outflow port to a jetting portion of the cap in a direction toward the visual field region in a position separated from the observation optical system,
wherein, in the longitudinal axis direction of the insertion part, the liquid guiding surface is disposed between the outflow port and a distal end of the cap,
wherein the liquid guiding surface is a bent flow path formed by an inner wall surface of a groove formed in the cap,
wherein the jetting portion is disposed on a base end of the cap in the longitudinal axis direction of the insertion part,
wherein the jetting portion is configured such that a jetting direction of the liquid is away from the observation optical system.

2. The endoscope according to claim 1,
wherein the cap has an inflow portion facing the outflow port in a state where the cap is attached to the distal end portion main body, the jetting portion that is open toward the visual field region, and a flow path connecting the inflow portion and the jetting portion to each other, and a wall surface of the flow path is formed as the liquid guiding surface.

3. The endoscope according to claim 2, wherein the jetting portion is configured such that a jetting direction is directed to a position separated from the observation optical system in an optical axis direction of the observation optical system.

4. The endoscope according to claim 2, wherein a position of the jetting portion in the longitudinal axis direction is located on a base end side in the longitudinal axis direction with respect to a position of the observation optical system in the longitudinal axis direction.

5. The endoscope according to claim 2, wherein a position of the jetting portion in the longitudinal axis direction is located on a distal end side in the longitudinal axis direction with respect to a position of the observation optical system in the longitudinal axis direction.

6. The endoscope according to claim 2, wherein the elevator housing portion and the observation optical system are disposed adjacent to each other in a second direction orthogonal to the longitudinal axis direction and orthogonal to the first direction, and the jetting portion is disposed on a side opposite to the observation optical system with the elevator housing portion interposed therebetween.

7. The endoscope according to claim 2, wherein the elevator housing portion and the observation optical system are disposed adjacent to each other in a second direction orthogonal to the longitudinal axis direction and orthogonal to the first direction, and the jetting portion is disposed on a side opposite to the elevator housing portion with the observation optical system interposed therebetween.

8. The endoscope according to claim 4, wherein the outflow port is configured such that an outflow direction is directed in a direction along the longitudinal axis direction.

9. The endoscope according to claim 6, wherein the outflow port is configured such that an outflow direction is directed in a direction along the second direction.

10. The endoscope according to claim 1, wherein the liquid guiding surface is formed by an inner wall surface of a through-hole formed in the cap.

* * * * *